United States Patent
Chalvignac (10) Patent No.: US 9,981,093 B2
(45) Date of Patent: *May 29, 2018

(54) PASSIVE GAS REGULATING VALVE FOR A RESPIRATORY SYSTEM

(71) Applicant: ResMed Paris SAS, Moissy-Cramayel (FR)

(72) Inventor: Philippe Auguste Chalvignac, Moissy Cramayel (FR)

(73) Assignee: ResMed Paris SAS (FR)

( * ) Notice: Subject to any disclaimer, the term of this patent is extended or adjusted under 35 U.S.C. 154(b) by 54 days.

This patent is subject to a terminal disclaimer.

(21) Appl. No.: 14/458,518

(22) Filed: Aug. 13, 2014

(65) Prior Publication Data

US 2014/0345617 A1 Nov. 27, 2014

Related U.S. Application Data

(63) Continuation of application No. 12/529,044, filed as application No. PCT/IB2007/001837 on Mar. 21, 2007, now Pat. No. 9,144,653.

(51) Int. Cl.
*A61M 16/00* (2006.01)
*A61M 16/10* (2006.01)
(Continued)

(52) U.S. Cl.
CPC ........ *A61M 16/00* (2013.01); *A61M 16/0003* (2014.02); *A61M 16/0069* (2014.02);
(Continued)

(58) Field of Classification Search
CPC .............. A61M 16/207; A61M 16/206; A61M 16/209; A61M 16/208; A61M 16/06; A61M 16/0069; A61M 16/00; Y10T 137/88054
(Continued)

(56) References Cited

U.S. PATENT DOCUMENTS 3,063,461 A * 11/1962 Rudolph .................. A62B 9/02
137/102
3,419,031 A 12/1968 Hesse et al.
(Continued)

FOREIGN PATENT DOCUMENTS

EP 0615764 B1 5/1999
EP 0990448 B9 11/2007
(Continued)

*Primary Examiner* — Tan-Uyen (Jackie) T Ho
*Assistant Examiner* — Jonathan Paciorek
(74) *Attorney, Agent, or Firm* — Lerner, David, Littenberg, Krumholz & Mentlik, LLP (57) ABSTRACT

The invention relates to a gas regulating valve (1) for a respiratory system comprising:—a main path between an inlet (2) and an outlet (3), and—an evacuation path between the outlet (3) and an evacuation orifice (4), characterised in that:—the main path is provided with at least a non-return valve for preventing gas to circulate from the outlet (3) to the inlet (2), and—the evacuation path is provided with an obstructing membrane (10) arranged and designed for being deformed by gas from the inlet (2) to partially or fully obstruct the evacuation path. The invention also relates to a mask integrating such gas regulating valve, and to a respiratory system also comprising such gas regulating valve.

19 Claims, 5 Drawing Sheets

(51) Int. Cl.
*A61M 16/20* (2006.01)
*A61M 16/06* (2006.01)

(52) U.S. Cl.
CPC ........ *A61M 16/06* (2013.01); *A61M 16/1005* (2014.02); *A61M 16/206* (2014.02); *A61M 16/207* (2014.02); *A61M 16/208* (2013.01); *A61M 16/209* (2014.02); *A61M 2016/003* (2013.01); *A61M 2016/0027* (2013.01); *A61M 2016/0036* (2013.01); *A61M 2016/1025* (2013.01); *A61M 2205/3368* (2013.01); *A61M 2230/435* (2013.01); *Y10T 137/7842* (2015.04); *Y10T 137/88054* (2015.04)

(58) Field of Classification Search
USPC ............ 128/202.28, 203.11, 204.18, 204.26, 128/205.24
See application file for complete search history.

(56) References Cited

U.S. PATENT DOCUMENTS

| | | | | |
|---|---|---|---|---|
| 3,556,122 | A | * | 1/1971 | Laerdal ............... A61M 16/208 128/205.24 |
| 3,889,670 | A | * | 6/1975 | Loveland ............... A61G 10/04 128/203.12 |
| 3,978,878 | A | | 9/1976 | Rudolph |
| 4,239,038 | A | * | 12/1980 | Holmes ............... A61M 16/208 128/205.13 |
| 4,373,520 | A | | 2/1983 | Arbique |
| 4,428,392 | A | | 1/1984 | Jones et al. |
| 4,590,951 | A | * | 5/1986 | O'Connor ............. A62B 18/006 128/201.25 |
| 4,694,825 | A | * | 9/1987 | Slemmer ............... A61M 16/20 128/205.24 |
| 4,873,972 | A | * | 10/1989 | Magidson ............ A62B 18/025 128/206.12 |
| 5,002,050 | A | * | 3/1991 | McGinnis ........... A61M 16/208 128/204.18 |
| 5,005,568 | A | | 4/1991 | Loescher et al. |
| 5,617,847 | A | | 4/1997 | Howe |
| 5,647,355 | A | * | 7/1997 | Starr ........................ A62B 7/12 128/205.24 |
| 6,306,114 | B1 | | 10/2001 | Freeman et al. |
| 2002/0170562 | A1 | | 11/2002 | Lurie et al. |
| 2002/0195105 | A1 | * | 12/2002 | Blue ..................... A61M 16/00 128/204.21 |
| 2004/0099266 | A1 | | 5/2004 | Cross et al. |
| 2008/0078395 | A1 | * | 4/2008 | Ho et al. .................. 128/205.24 |
| 2009/0032022 | A1 | | 2/2009 | Ho et al. |
| 2009/0205662 | A1 | * | 8/2009 | Kwok et al. ............. 128/204.23 |

FOREIGN PATENT DOCUMENTS

| | | |
|---|---|---|
| FR | 2535613 A1 | 5/1984 |
| JP | 39-037479 Y1 | 12/1964 |
| JP | 44-028557 Y1 | 11/1969 |
| JP | 06-504922 | 6/1994 |
| JP | 07-000516 A | 1/1995 |
| JP | 2000-060974 A | 2/2000 |
| JP | 2002-533174 A | 10/2002 |
| WO | 9206728 A1 | 4/1992 |
| WO | 0038772 A1 | 7/2000 |
| WO | 2006117379 A2 | 11/2006 |

* cited by examiner

PASSIVE GAS REGULATING VALVE FOR A RESPIRATORY SYSTEM

CROSS-REFERENCE TO RELATED APPLICATIONS

The present application is a continuation of U.S. patent application Ser. No. 12/529,044, filed Aug. 28, 2009, which is a national phase entry under 35 U.S.C. § 371 of International Application No. PCT/IB07/01837 filed March 21, 2007, published in English which are hereby incorporated herein by reference.

FIELD OF THE INVENTION

The present invention relates to a gas regulating valve for a respiratory system.

It further relates to a respiratory system comprising said gas regulating valve, for a patient breathing in successive respiratory cycles, each respiratory cycle being defined by at least an inspiration phase and at least an expiration phase.

BACKGROUND OF THE INVENTION

Ventilation of a patient involves the delivery of a breathable gas (typically ambient air to which a complementary gas such as oxygen can be added) pressurised above atmospheric pressure to a patient via a conduit, and a mask or tracheotomy tube.

There are an increasing number of disorders that require assisted and/or controlled ventilation of the patient. It is namely common to use breathing assistance devices for diseases where mechanical ventilation is needed, for example in neuromuscular disease where volume controlled ventilation is required. These devices may also be used for other respiratory diseases or disorders, such as for providing continuous positive airway pressure treatment for obstructive sleep apnea.

For either application of assisted and/or controlled ventilation, the pressure of the gas delivered to patients can be constant level, bi-level (in synchronism with patient breathing) or auto-adjusting in level. This enables controlling the Positive Expiratory Pressure (PEP) to remain equal to the expiratory pressure of the patient, so that the residual overpressure in the patient lungs is balanced. Throughout this specification reference to gas supply unit is intended to incorporate a reference to any one of, or combinations of, these forms of pressurised gas supply.

It is desirable to minimize the size of the respiratory system for increasing the mobility and comfort of the patient. It is also sought to have a respiratory system which may be used in a variety of places and circumstances (e.g. home or hospital), and which therefore needs to be both simple and reliable.

It has thus been proposed to use a respiratory system including a gas supply unit connected to an electromagnetic gas regulating valve via a single gas conduit. Such valves are described in the PCT application published on Nov. 9, 2006 under the reference WO 2006/117379, which is incorporated herein by reference in its entirety. With such gas regulating valves, the gas supply unit of the respiratory system can be reduced in size, and a single gas conduit is needed which eases movement of the patient. However, such an electromagnetic valve is heavy which is not comfortable for the patient. This kind of valve is also quite expensive as it is made with uncommon elements and is quite complex to manufacture.

Therefore, it is an object of the present invention to provide a gas regulating valve that substantially overcomes or at least ameliorate one or more of the above deficiencies.

BRIEF SUMMARY OF THE INVENTION

A first aspect of the invention is to provide a gas regulating valve which is very simple to manufacture, with well known elements, in a cheap and light manner.

A further aspect of the invention is to provide a passive gas regulating valve which may be used with most gas supply units and which does not require a complex controller for managing its operation.

A further aspect of the invention is to provide a passive gas regulating valve which is reliable and safe for the user.

In one form the invention proposes a gas regulating valve as defined in claim 1.

In a preferred embodiment, the invention concerns a gas regulating valve for a respiratory system comprising:
  a main path between an inlet and an outlet, and
  an evacuation path between the outlet and an evacuation orifice, characterised in that:
    the main path is provided with at least a non-return valve for preventing gas to circulate from the outlet to the inlet, and
    the evacuation path is provided with an obstructing membrane arranged and designed for being deformed by gas from the inlet to partially or fully obstruct the evacuation path.

Preferable but not limited aspects of such a gas regulating valve are the following:
  the obstructing membrane has the form of an inflatable balloon having an aperture oriented towards the inlet;
  the main path and the evacuation path are coaxial;
  the main path comprises two lateral channels and the evacuation path comprises a central channel, the lateral channels running in parallel to the central channel;
  the main path comprises two non-return valves, each non-return valve being located in a distinct lateral channel;
  a small aperture is provided on at least one of the non-return valves, preferably on both non-return valves;
  the main path further comprises a security orifice provided with a security valve, the security valve being adapted to allow passage of gas from outside of the main path to the outlet through the security orifice when a positive pressure difference occurs between the pressure outside the main path and the pressure inside;
  the gas regulating valve may further comprise a printed circuit board connected to sensors arranged for sensing the gas at the outlet;
  the sensors include a gas flow sensor, a pressure sensor, an oxygen sensor and/or a temperature sensor.

According to a further aspect of the invention, the gas regulating valve is made integral with a mask so that it may be disposed directly at the mouth of the patient.

According to still a further aspect of the invention, there is proposed a respiratory system for supplying a patient breathing in successive cycles with pressurised gas, each cycle being defined by at least an inspiration phase and at least an expiration phase, comprising a gas supply unit and the above described gas regulating valve, the inlet of the gas regulating valve being connected to the gas supply unit with a single gas conduit, and the outlet of the gas regulating valve being connected to the patient, wherein pressurised gas in conveyed from the gas supply unit to the patient through the gas regulating valve during inspiration phases, and wherein gas expelled from the patient during expiration phases is evacuated from the outlet through the evacuation orifice.

Preferable but not limited aspects of such a respiratory system are the following:

the gas supply unit supplies a flow of gas for controlling obstruction of the evacuation path by the obstructing membrane so that positive expiratory pressure (PEP) remains equal to expiration pressure;

the pressure sensor provided in the gas regulating valve is arranged for measuring expiration pressure of the patient so that the positive expiratory pressure (PEP) is precisely controlled with the gas supply unit.

BRIEF DESCRIPTION OF THE DRAWINGS

Other characteristics and advantages of the invention will become clear from the following description which is only given for illustrative purposes and is in no way limiting and should be read with reference to the attached drawings in which.

DETAILED DESCRIPTION

As explained above, one major evolution in the miniaturization of respiratory systems resides in the use of a gas regulating valve that avoids using several gas conduits for circulation of gas, and that also enables simplification of the respiratory system per se.

The passive gas regulating valve that is described below is based on this concept of providing an evacuation orifice for expiratory gases in a single gas regulating valve that is located at or near the mouth of the patient, so that the expiratory gases do not remained accumulated within the gas conduit and are directly evacuated outside the respiratory system, preferably to the atmosphere. The gas regulating valve must however be adapted for managing circulation of gas in both the inspiration and expiration phases, that is for allowing circulation of gas from a gas supply unit to the patient, and from the patient to the atmosphere respectively.

Figure 1:
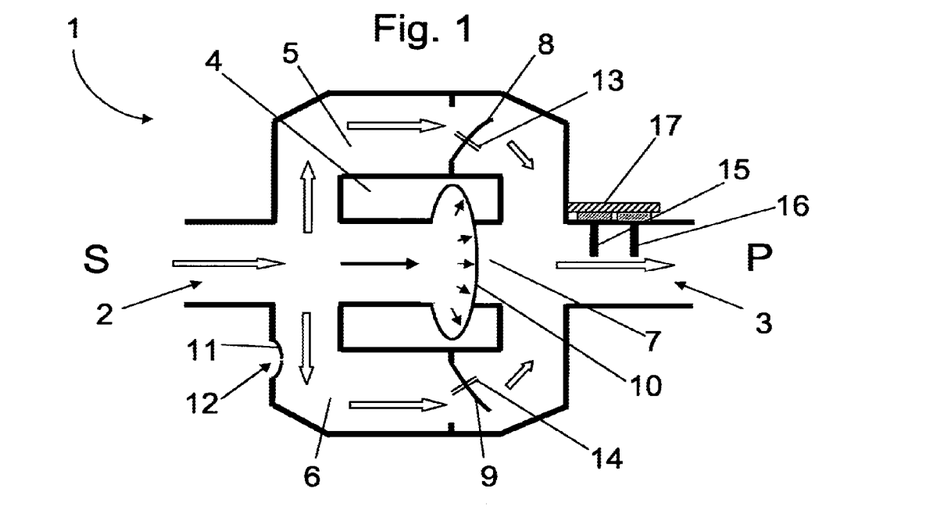
FIG. 1 is a schematic representation of a passive gas regulating valve during an inspiration phase.
Figure 2:
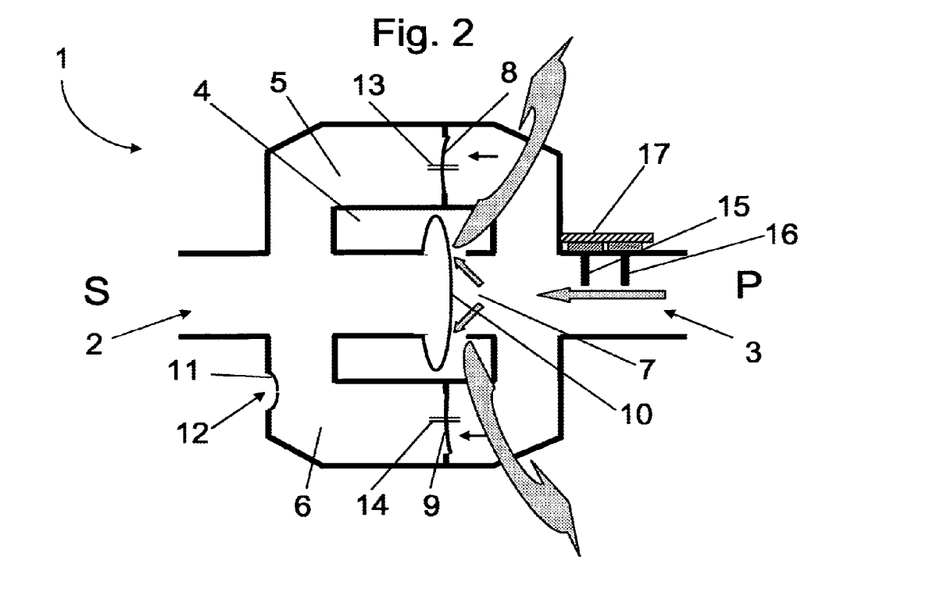
FIG. 2 is a schematic representation of a passive gas regulating valve during an expiration phase.
Figure 3:
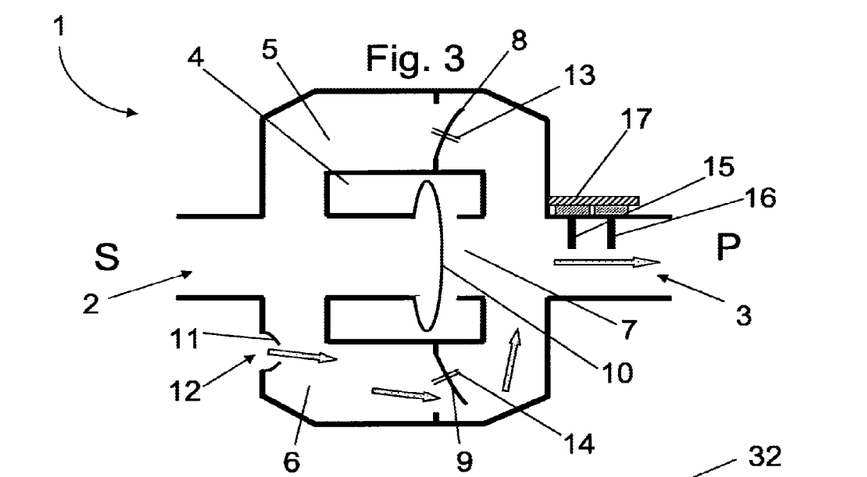
FIG. 3 is a schematic representation of a passive gas regulating valve during an expiration phase, in case of breakdown of the gas supply unit.
Figure 4:
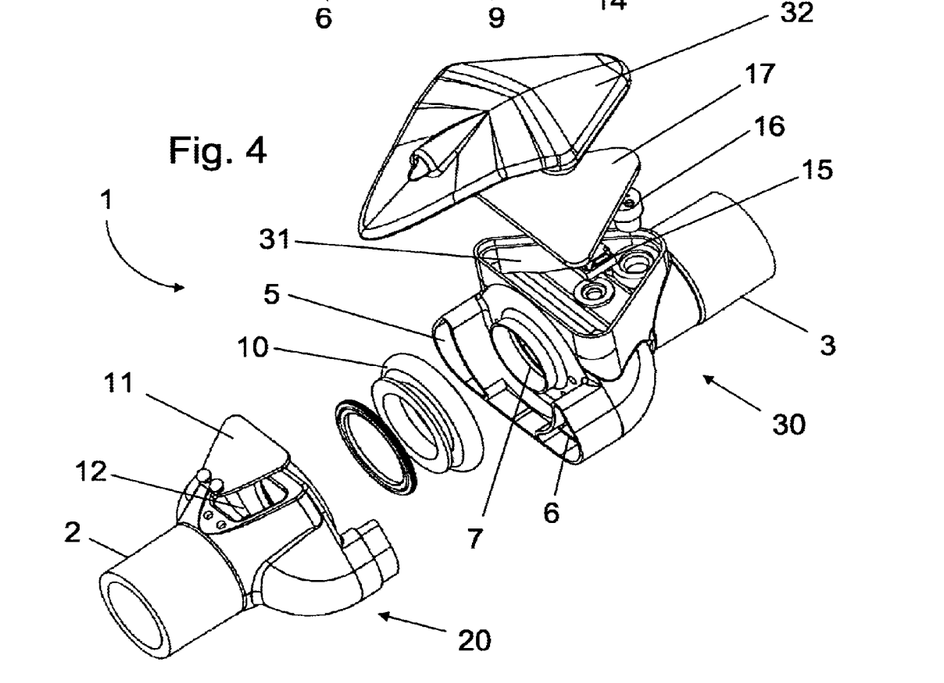
FIG. 4 is a three-dimensional exploded view of a passive regulating valve according to an embodiment of the invention.
Figure 5:
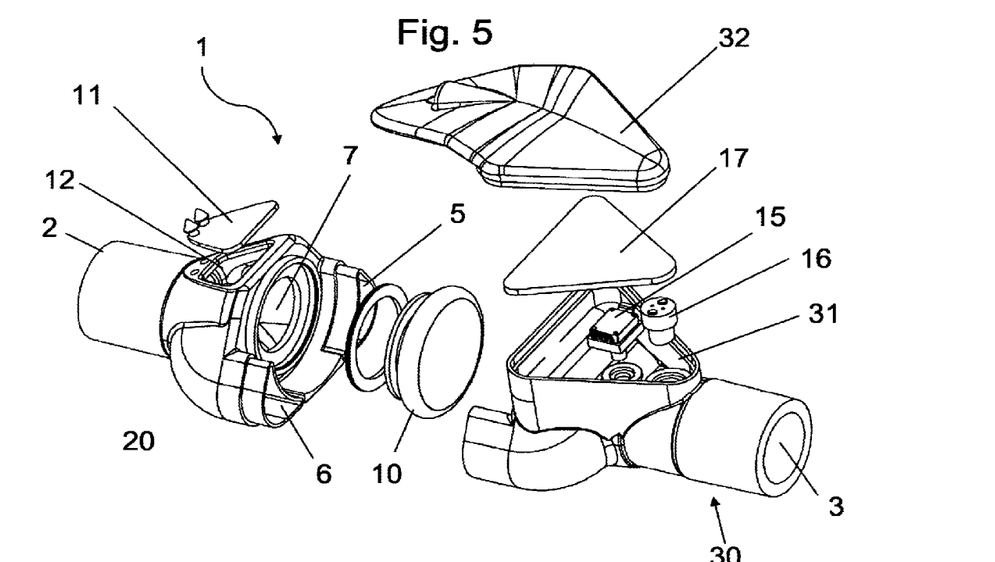
FIG. 5 is another three-dimensional exploded view of the passive regulating valve of FIG. 3.
Figure 6:
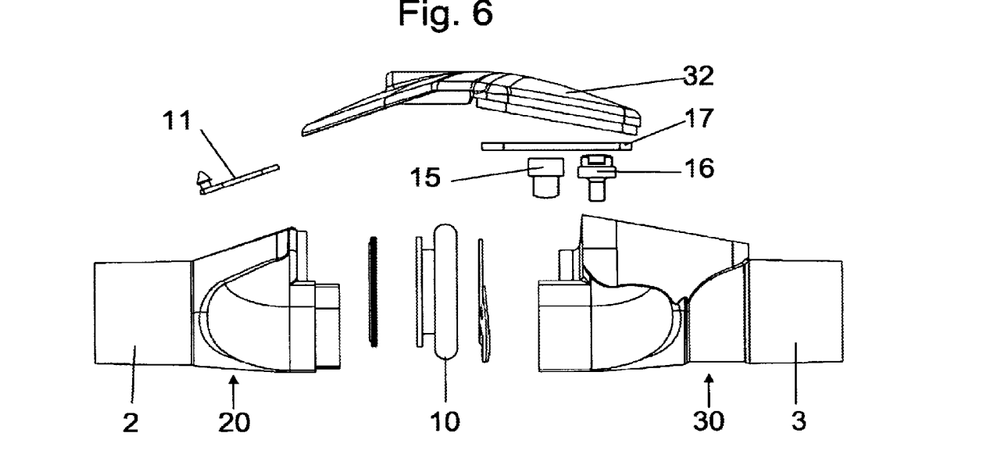
FIG. 6 is a side exploded view of the passive regulating valve of FIG. 3.
Figure 7:
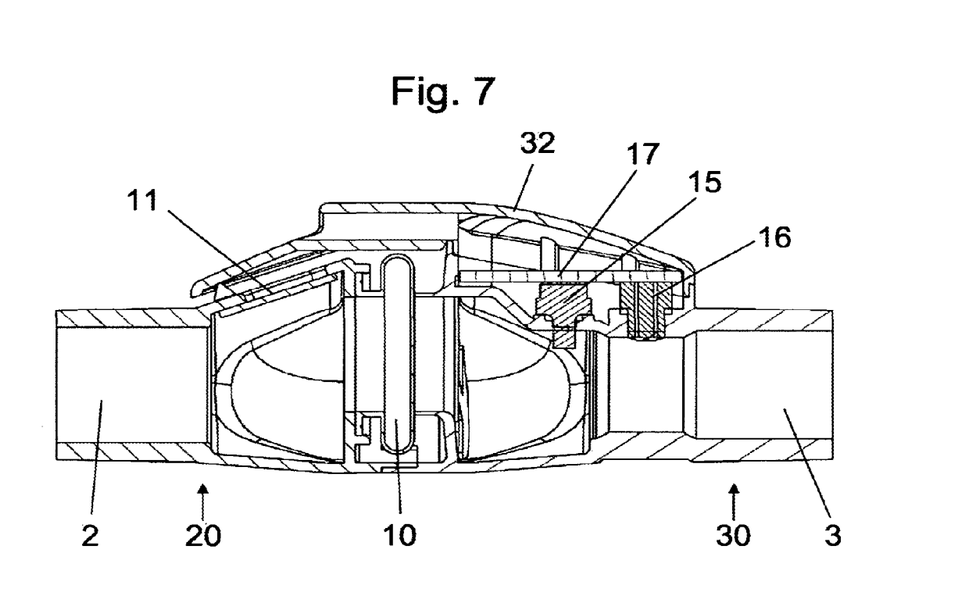
FIG. 7 is a side sectional view of the passive regulating valve of FIG. 3.
Figure 8:
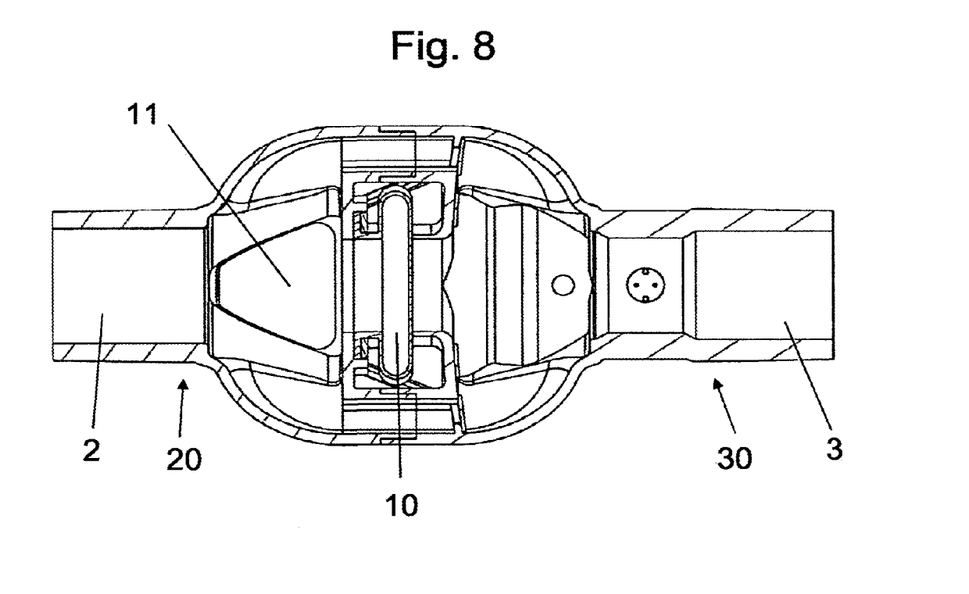
FIG. 8 is a top sectional view of the passive regulating valve of FIG. 3.

The passive gas regulating valve 1 that is schematically represented in FIGS. 1, 2, and 3 is designed for enabling such an operation in a simple manner, with a valve that could be manufactured in a relatively cheap manner.

The passive gas regulating valve 1 is designed so that it comprises a main path from an inlet 2 to an outlet 3. This main path is illustrated by the white arrows depicted in FIG. 1. When the gas regulating valve 1 is coupled at the inlet 2 to a gas supply unit, called gas source S, and coupled at the outlet 3 to a patient P, this main path allows the pressurised gas to circulate from the gas source S to the patient P during inspiration phases.

As depicted in FIG. 2 by the dotted arrows, the gas regulating valve also comprises an evacuation path between the outlet 3 and one or more evacuation orifice(s) 4. This evacuation path allows the expiratory gases expelled by the patient P at the outlet 3 to be evacuated outside the gas regulating valve 1 through the evacuation orifice 4, preferably directly in the atmosphere.

Both main and evacuations paths therefore have a common portion, at the outlet 3, which facilitates a reduction in the global volume of the gas regulating valve 1. Furthermore, both paths preferably run substantially in parallel to further optimise the global volume of the gas regulating valve 1.

For instance, the main path may comprise two channels (5;6) from the inlet 2 to the outlet 3, these two channels being arranged parallel to a central channel 7 used for the evacuation path from the outlet 3 to the evacuation orifice 4. This particular arrangement may also be inverted by designing the valve 1 so that the main path comprises a central channel from the inlet 2 to the outlet 3 and the evacuation path comprises at least one, preferably two channels arranged adjacent the main channel from the outlet 3 to evacuation orifices 4.

As the main path and the evacuation path have a common portion, it is necessary to provide the gas regulating valve with blocking elements so that the main path is active during inspiration phases, whereas the evacuation path is active only during expiration phases.

The evacuation path should comprise an obstruction element for preventing the gas circulating inside the gas regulating valve to be evacuated during inspiration phases, but allowing such evacuation to the atmosphere for example, during expiration phases. To this end, there is provided a membrane 10 in the channel 7 of the evacuation path from the outlet 3 to the evacuation orifice 4, this membrane being arranged in such a manner that it may be deformed by gas arriving from the inlet 2, in order to obstruct partially or fully the central channel 7 for blocking the evacuation path. To this end, the dimensions of the membrane should be larger than the dimensions, of the central channel 7, in particular the diameter of the membrane 10 should be larger than the diameter of the central channel 7.

In a preferred embodiment, this membrane has the form of a balloon 10 whose opening is oriented towards the inlet 2, so that the balloon may be inflated by gas arriving from the inlet 2. This obstruction 10 element may be made in an elastic material such as rubber or silicon.

Preferably, the main path also comprises a non-return valve allowing only circulation of gas from the inlet 2 to the outlet 3, and not from the outlet 3 to the inlet 2. If the main path comprises several channels running in parallel, each channel should preferably be provided with a non-return valve, as depicted in FIGS. 1, 2, and 3, where the main path comprises two channels (5;6), each of which comprises a respective non-return valve (8;9).

With such an arrangement, the gas regulating valve operates properly during both inspiration and expiration phases.

Indeed, during inspiration phases, as illustrated in FIG. 1, gas is conveyed from a gas source and enters the gas regulating valve 1 through the inlet 2. Then this gas arrives in the lateral channels (5;6) and opens the non-return valves (8;9) to reach the outlet 3 of the gas regulating valve 1 (see the white arrows on FIG. 1).

At the same time the gas from the inlet 2 circulates in the central channel 7 into the balloon 10 to inflate the balloon, as it is depicted by the black arrows in FIG. 1. Inflation of the balloon 10 causes the evacuation path to be obstructed as the balloon 10 closes every passage to the evacuation orifices. As a consequence, the gas that circulates from the inlet 2 in the main path can only reach the outlet 3, and will not be evacuated to the atmosphere. Then the patient P can inspire the delivered gas at the outlet 3, via a gas conduit, and a mask or tracheotomy tube.

During expiration phases, as illustrated in FIG. 2, the patient P expels expiratory gases through a gas conduit to the outlet 3. Such expiratory gases must be evacuated outside the gas regulating valve, for example to the atmosphere, which is possible by activating gas flow to the evacuation path and deactivating gas flow to the main path.

As depicted by the black arrows on FIG. 2, the gas cannot circulate from the outlet 3 to the inlet 2 through the lateral channels (5;6) as the non-return valves (8;9) prevent such circulation. The non-return valves may consist in flaps that are closed by the gas arriving from the outlet 3, thus deactivating gas flow through the main path.

At the same time, the gas from the outlet 3 passes in the central channel 7 and forces the membrane 10 to be deformed in a manner that allows gas to reach the evacuation orifices 4 to exit the gas regulating valve 1 (see the dotted arrows on FIG. 2). In the case where the obstructing membrane 10 is a balloon, the balloon is deflated by the gas arriving from the outlet 3 to facilitate reopening of the passage to the evacuation orifices.

As already mentioned the obstructing membrane 10, having the form of a balloon or not, is preferably made in an elastic material and arranged so that a passage between the outlet 3 and the evacuation orifices 4 remains open when the membrane is not constrained. This would allow the patient to expire more easily. This may also allow the patient to inspire air from the atmosphere through the evacuation orifices 4 in case of breakdown of the gas source S. In this latter case, the membrane 10 should be sufficiently elastic so as to allow deformation of the membrane 10 to allow a patient to inspire but to prevent the membrane 10 from obstructing the central channel 7 because of the inspiration of the patient P.

To ensure inspiration of the patient P even when the gas source breaks down, a security valve 11 may be provided in the gas regulating valve 1. Such security valve 11 is arranged for obstructing an orifice 12, called a security orifice, between the main path and the atmosphere. This valve 11, which may be a flap, is adapted to allow passage of gas from outside the main path to the outlet 3 through the security orifice 12 when there is a positive difference between the pressure outside the main path and the pressure inside the main path. As a consequence, if the gas source S breaks down (as illustrated in FIG. 3), the patient P will try to inspire during inspiration phases, thus creating a depression which would open the security valve 11 so that the patient P can inspire air from the atmosphere.

According to another embodiment of the gas regulating valve 1, one or both of the flaps (8;9) forming the non-return valves of the lateral channels (5;6) of the main path comprise(s) a through-aperture (13;14), which is small relative to the size of the corresponding flap (8;9).

Such apertures (13;14) are arranged for balancing pressure on both side of the valve during expiration phases. These apertures (13;14) further avoid the flaps (8;9) forming the non-return valves from vibrating, particularly at the transition between the expiration and the inspiration phases. Vibration of the balloon may also be prevented with the use of such apertures (13;14).

According to a further embodiment, the gas regulating valve 1 comprises sensors for sensing the flow of gas within the valve 1. These sensors are preferably arranged to sense the flow of gas at the outlet 3. Thus, there is preferably provided a gas flow sensor 15, such as a hot wire sensor, and a pressure sensor 16. Other sensors may also be provided such as an oxygen sensor for sensing the amount of oxygen within the flow of pressurised gas, and/or a temperature sensor.

With the data collected by these sensors, it is possible to monitor the patient breathing. As will be explained in more detail below, theses sensors could also be used for adequately controlling the gas supply unit, for example to supply more or less gas to the inlet 2, depending on the phase of the breathing cycle.

Preferably, the sensors are connected to a printed circuit board 17 as illustrated in FIGS. 1, 2, and 3. The printed circuit board 17 gathers the data collected from the different sensors. This facilitates having a simple electrical connection between the gas regulating valve 1 and the corresponding gas supply unit that generally comprises a controller for controlling supply of gas.

FIGS. 4 to 8 represent a particular embodiment of such a passive gas regulating valve 1. For ease of understanding, it has been chosen to keep the same numerical references of FIGS. 1 to 3 for the common elements.

This gas regulating valve is made of two main casings (20;30), an inlet casing 20 and an outlet casing 30. The inlet casing comprises the inlet 2 and the outlet casing comprises the outlet 3. Each of the inlet and outlet casings (20;30) also comprise a portion of the central channel 7 and the lateral channels (5;6). The inlet and outlet casings (20;30) are coupled together by interlocking the different portions of the lateral channels (5;6) with each other to form the complete central channel 7 and lateral channels (5;6).

Between the two portions of the central channel 7 is interposed the elastic membrane 10 which preferably has the form of a balloon. The membrane 10 is preferably attached to the central channel portion of the inlet casing 20. When the balloon 10 is inflated, it closes the portion of the central channel 7 of the outlet casing 30. If the balloon 10 is not inflated, the portion of the central channel 7 of the outlet casing 30 is opened towards the atmosphere.

The outlet casing 30 comprising the outlet 3 is further designed to comprise a housing 31 wherein the sensors (15;16) are plugged in order to sense the flow of gas at the outlet 3. This housing 31 is further designed for enclosing a printed circuit board 17 that may be connected to a controller provided in a gas supply unit for example. A cover 32 may also be provided for protecting the components enclosed in the housing 31 and also to protect the balloon 10 interposed in the central channel 7.

Finally, the inlet casing 20 comprising the inlet 2 comprises a security aperture 12 provided with a security flap 11 for preventing any asphyxia of the patient, for example in case of breakdown of the gas source S.

Advantageously such a valve is made of quite simple components, easy to manufacture, and easy to mount or dismount. In particular the valve is designed to facilitate easy cleaning of the valve, or replacement of only one of its components. For example it would be possible to sterilise, for example with an autoclave, only the components that have been polluted by the gas flow, while preserving and reusing the others, such as the printed circuit board 17.

Figure 9:
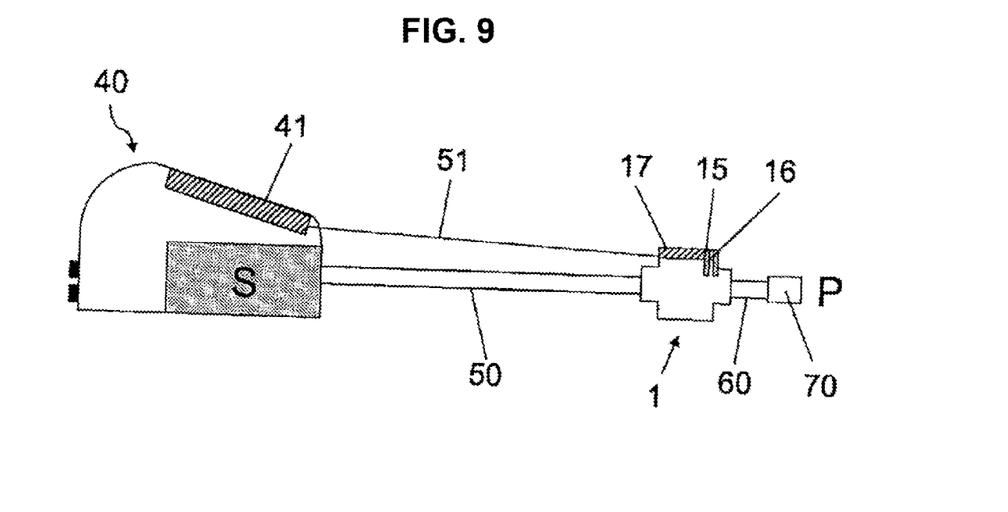
FIG. 9 is a schematic representation of a respiratory system comprising a passive regulating valve.

As illustrated in FIG. 9, the passive gas regulating valve 1 may be used with a gas supply unit 40 to form a respiratory system adapted for supplying pressurised gas to a patient P. To this end, the gas supply unit 40 is coupled to the inlet 2 of the gas regulating valve 1 with a single gas conduit 50.

The gas supply unit 40 further comprises a controller 41 which may be connected to the printed circuit board 17 of the gas regulating valve 1 via an electric wire 51, in order to integrate data from the sensors (15;16) of the gas regulating valve 1 and adequately controls the flow of pressurised gas to be supplied to the gas regulating valve 1 by the gas source S. In an alternative embodiment the printed circuit board 17 may communicate with the controller 41 via wireless communication systems such as bluetooth or infrared communication. Thus removing the requirement for electric wire 51.

The outlet 3 of the gas regulating valve 1 is coupled to the patient P via a gas conduit 60, and a mask or tracheotomy tube 70. The gas regulating valve 1 may also be integrated within the mask to form a single component, and therefore increase the comfort of the respiratory system.

In a preferred embodiment the pressure mode of the gas delivered by the gas supply unit 40 is bi-level.

According to a first embodiment, the gas supply unit 40 supplies pressurised gas to the gas regulating valve 1 only during inspiration phases in order to fully close the evacuation path. During expiration phases, no gas, or substantially no gas, is supplied by the gas supply unit 40 so that the expiratory gases are freely evacuated to the atmosphere through the evacuation path.

According to a second embodiment, the gas supply unit 40 continuously supplies pressurised gas, but in synchronism with the patient breathing. The level during inspiration phases is the same as in the first embodiment. However, during expiration phases, pressurised gas is supplied at a lower pressure than that provided during inspiration phases, in order to control the level of inflation of the balloon 10 to control opening of the evacuation orifice, and therefore control leakage of the expiratory gases through the evacuation path. This enables controlling the Positive Expiratory Pressure (PEP) to remain equal to the expiratory pressure of the patient, so that the residual overpressure in the patient lungs is balanced.

As a consequence, the passive expiratory valve 1 can be used in any type of respiratory system. This valve has the further advantage of being very simple to manufacture, to mount and dismount for cleaning purposes for example, and remains very reliable for a user, even in the case of breakdown of the gas source.

The reader will have understood that many modifications may be made without going beyond the new information and the advantages described herein. Consequently, all modifications of this type shall be within the scope of the gas regulating valve and respiratory system as defined in the attached claims.

The invention claimed is:

1. A gas regulating valve for a respiratory system comprising:
   a main path between an inlet and an outlet, and
   an evacuation path between the outlet and an evacuation orifice, wherein:
   the main path is provided with at least a non-return valve for preventing gas to circulate from the outlet to the inlet,
   the evacuation path is provided with an obstructing membrane, the obstructing membrane including a central deformable portion for operatively closing, at least partially, the evacuation orifice in response to gas flow from the inlet,
   the gas regulating valve includes a central channel leading from a gas supply unit to the obstructing membrane, the central channel being sealed by the membrane at one end so as to prevent gas transfer through the central channel for inspiration when in use, and
   the central deformable portion is configured to respond to pressure generated from the gas supply unit in the central channel so as to expand the membrane so that the membrane blocks the evacuation path at the evacuation orifice, and is configured to retract so as to open the evacuation orifice when a gas flow is received from the outlet along the evacuation path.

2. The gas regulating valve of claim 1, wherein the obstructing membrane has a form of an inflatable balloon having an aperture oriented towards the inlet.

3. The gas regulating valve of claim 1, wherein the main path and the evacuation path are coaxial.

4. The gas regulating valve of claim 3, wherein the main path comprises two lateral channels and the evacuation path comprises an evacuation channel, the lateral channels running in parallel to the evacuation channel.

5. The gas regulating valve of claim 4, wherein the main path comprises two non-return valves, wherein one of the two non-return valves is located in one of the two lateral channels and a second of the two non-return valves is located in a second of the two lateral channels.

6. The gas regulating valve of claim 5, wherein an aperture is provided on at least one of the non-return valves.

7. The gas regulating valve of claim 6, wherein an aperture is provided on both non-return valves.

8. The gas regulating valve of claim 1, wherein the main path further comprises a security orifice provided with a security valve, the security valve being adapted to allow passage of gas from outside of the main path to the outlet through the security orifice when a positive pressure difference occurs between the pressure outside the main path and the pressure inside.

9. The gas regulating valve of claim 1, further comprising a printed circuit board connected to sensors arranged for sensing the gas at the outlet.

10. The gas regulating valve of claim 9, wherein the sensors include a gas flow sensor, a pressure sensor, an oxygen sensor and/or a temperature sensor.

11. A mask for supplying a patient with pressurized gas, wherein said mask integrates a gas regulating valve as claimed in claim 1.

12. A respiratory system for supplying a patient breathing in successive cycles with pressurized gas, each cycle being defined by at least an inspiration phase and at least an expiration phase, comprising a gas supply unit and a gas regulating valve, wherein
   the gas regulating valve comprises a main path between an inlet and an outlet, and an evacuation path between the outlet and an evacuation orifice, wherein:
   the main path is provided with at least a non-return valve for preventing gas to circulate from the outlet to the inlet,
   the evacuation path is provided with an obstructing membrane, the obstructing membrane including a central deformable portion for operatively closing the evacuation orifice in response to gas flow from the inlet, the inlet of the gas regulating valve is connected to the gas supply unit with a single gas conduit, and the outlet of the gas regulating valve is connected to the patient, wherein pressurized gas is conveyed from the gas supply unit to the patient through the gas regulating valve during inspiration phases, and wherein gas expelled from the patient during expiration phases is evacuated from the outlet through the evacuation orifice, the gas regulating valve includes a central channel leading from the gas supply unit to the obstructing membrane, the central channel being sealed by the membrane at one end so as to prevent gas transfer through the central channel for inspiration when in use, and the central deformable portion is configured to respond to pressure generated from the gas supply unit in the central channel so as to expand so that the membrane blocks the evacuation path at the evacuation orifice, and is configured to retract so as to open the evacuation orifice when a gas flow is received from the outlet along the evacuation path.

13. The respiratory system of claim 12, wherein the gas supply unit supplies a flow of gas for controlling obstruction of the evacuation path by the obstructing membrane so that a residual overpressure in lungs of the patient is balanced.

14. The respiratory system of claim 13, wherein the gas regulating valve includes a pressure sensor arranged for measuring expiration pressure of the patient so that positive expiratory pressure (PEP) is precisely controlled with the gas supply unit.

15. The respiratory system of claim 12, wherein the central deformable portion is configured to retract absent the pressure from the gas supply unit so as to open the evacuation orifice.

16. The gas regulating valve of claim 1 wherein the central deformable portion is configured to retract absent the pressure from the gas supply unit so as to open the evacuation orifice.

17. The mask of claim 11, wherein the central deformable portion is configured to retract absent the pressure from the gas supply unit so as to open the evacuation orifice.

18. A passive gas regulating valve assembly for a respiratory mask supplying a patient with pressurized gas comprising:

an inlet casing comprising an inlet, a first portion of a central channel, a first portion of at least two lateral gas flow channels, and a security aperture with a security flap for preventing asphyxiation of a patient;

an outlet casing comprising an outlet, a second portion of the central channel, a second portion of the at least two lateral gas flow channels, and a housing for enclosing at least one sensor for measuring flow of gas at the outlet and for enclosing a printed circuit board;

an elastic membrane interposed between the inlet and outlet casings such that the first portion of the central channel is sealed by the elastic membrane at one end so as to prevent gas transfer through the central channel for inspiration when in use, wherein the elastic membrane comprises a central deformable portion for operatively closing an evacuation orifice when gas flows from the inlet, and wherein the central deformable portion is configured to respond to pressure generated from a gas supply unit in the first portion of the central channel so as to expand the elastic membrane so that the membrane blocks an evacuation path at the evacuation orifice, and is configured to retract so as to open the evacuation orifice when a gas flow is received from the outlet along the evacuation path; and a cover for protecting the at least one sensor and the printed circuit board enclosed in the housing and for protecting the elastic membrane, wherein the inlet and outlet casings are coupled together, in part, by interlocking the first and second portions of the at least two lateral gas flow channels; and wherein the at least two lateral channels both include non-return valves for preventing gas flow from the outlet to the inlet and permitting gas flow from the inlet to the outlet.

19. The passive gas regulating valve assembly of claim 18 wherein the central deformable portion is configured to retract absent the pressure from the gas supply unit so as to open the evacuation orifice.

* * * * *